US012208192B2

(12) United States Patent
Byhmer et al.

(10) Patent No.: US 12,208,192 B2
(45) Date of Patent: Jan. 28, 2025

(54) OPTICAL METHOD AND DEVICE FOR MONITORING A MEASUREMENT OBJECT

(71) Applicant: ODINWELL AB, Halmstad (SE)

(72) Inventors: Patrik Byhmer, Halmstad (SE); Patrik Strömsten, Mölnlycke (SE)

(73) Assignee: ODINWELL AB, Halmstad (SE)

( * ) Notice: Subject to any disclaimer, the term of this patent is extended or adjusted under 35 U.S.C. 154(b) by 432 days.

(21) Appl. No.: 17/635,857

(22) PCT Filed: Sep. 1, 2020

(86) PCT No.: PCT/SE2020/050828
§ 371 (c)(1),
(2) Date: Feb. 16, 2022

(87) PCT Pub. No.: WO2021/045665
PCT Pub. Date: Mar. 11, 2021

(65) Prior Publication Data
US 2022/0299442 A1    Sep. 22, 2022

(30) Foreign Application Priority Data

Sep. 2, 2019   (SE) .................................... 1930277-7

(51) Int. Cl.
*G01N 21/64*   (2006.01)
*A61M 1/36*    (2006.01)
(Continued)

(52) U.S. Cl.
CPC ....... *A61M 1/3656* (2014.02); *G01N 21/6428* (2013.01); *G01R 15/22* (2013.01);
(Continued)

(58) Field of Classification Search
CPC ............. H10K 50/84; H10K 2102/311; H10K 59/131; H10K 59/873; H10K 77/111;
(Continued)

(56) References Cited

U.S. PATENT DOCUMENTS

| 4,144,452 A | 3/1979 | Harte |
| 5,217,875 A | 6/1993 | Karpf et al. |

(Continued)

FOREIGN PATENT DOCUMENTS

| JP | 2010-216959 A | 9/2010 |
| WO | WO 92/05441 | 4/1992 |

(Continued)

OTHER PUBLICATIONS

Ferrari, Vittorio; "Distortion-free probes of electric field", Nature Electronics 1, 10-11 (2018).
(Continued)

*Primary Examiner* — Sang H Nguyen
(74) *Attorney, Agent, or Firm* — Birch, Stewart, Kolasch & Birch, LLP

(57) ABSTRACT

A method and device for monitoring a measurement object. A passive unit has a light source, which radiates radiated light modulated by at least one external measurement influence from the measurement object. An active unit has an optical detector, which receives the radiated and modulated light via an optical link. In addition, there is a transmitter unit emitting energy, such as optical energy, sound energy, electromagnetic energy etc. The emitted energy is coded by an energy signature and sent to the passive unit via an energy link. The passive unit receives the emitted energy by a receiver unit, which decodes the energy signature and moderates the radiated and modulated light in dependence of the energy signature. The received energy is also used to drive the light source. A processor unit may decode the signal for discriminating the signal from error sources.

11 Claims, 11 Drawing Sheets

(51) Int. Cl.
    *G01R 15/22* (2006.01)
    *A61M 1/00* (2006.01)
(52) U.S. Cl.
    CPC ............. *A61M 1/982* (2021.05); *A61M 1/985* (2021.05); *G01N 2021/6432* (2013.01)
(58) Field of Classification Search
    CPC ............... G01N 21/95; G01N 21/8422; G01N 21/6428; G01N 2021/6432; A61M 1/3656; A61M 1/982; A61M 1/985; G01R 15/22
    See application file for complete search history.

(56) References Cited

U.S. PATENT DOCUMENTS

| | | | | |
|---|---|---|---|---|
| 5,790,293 | A * | 8/1998 | Frigo | H04B 10/077 398/201 |
| 5,943,461 | A * | 8/1999 | Shahid | G02B 6/421 285/24 |
| 6,348,986 | B1 * | 2/2002 | Doucet | H01B 11/22 398/128 |
| 7,154,599 | B2 | 12/2006 | Adams et al. | |
| 7,670,289 | B1 | 3/2010 | McCall | |
| 2003/0128125 | A1 | 7/2003 | Burbank et al. | |
| 2005/0019031 | A1 * | 1/2005 | Ye | H04B 10/077 398/19 |
| 2005/0038325 | A1 | 2/2005 | Moll | |
| 2006/0130591 | A1 | 6/2006 | Perkins | |
| 2007/0280695 | A1 * | 12/2007 | Li | H04J 14/0305 398/135 |
| 2008/0089692 | A1 * | 4/2008 | Sorin | H04J 14/02 398/135 |
| 2008/0195060 | A1 | 8/2008 | Roger et al. | |
| 2009/0202194 | A1 | 8/2009 | Bosselmann et al. | |
| 2012/0296279 | A1 | 11/2012 | Muller et al. | |
| 2013/0203043 | A1 | 8/2013 | Ozcan et al. | |
| 2016/0305984 | A1 * | 10/2016 | Bohnert | G01R 15/247 |
| 2017/0065178 | A1 | 3/2017 | Suzuki et al. | |
| 2019/0255243 | A1 | 8/2019 | Byhmer et al. | |
| 2021/0293710 | A1 * | 9/2021 | Byhmer | G01N 21/645 |

FOREIGN PATENT DOCUMENTS

| | | |
|---|---|---|
| WO | WO 2013/147670 A1 | 10/2013 |
| WO | WO 2015/136956 A1 | 9/2015 |

OTHER PUBLICATIONS

Hect et al. "A low-cost optode-array measuring system based on 1 mm plastic optical fibers—new technique for in situ detection and quantification of pyrite weathering processes", Sensors and Actuators B 81 (2001), pp. 76-82.

The Extended European Search Report for PCT/SE2019/050721, mailed on Mar. 31, 2022.

International Search Report, issued in PCT/SE2020/050828, dated Oct. 28, 2020.

Written Opinion of the International Searching Authority, issued in PCT/SE2020/050828, dated Oct. 28, 2020.

Extended European Search Report for European Application No. 20861612.8, dated Sep. 11, 2023.

* cited by examiner

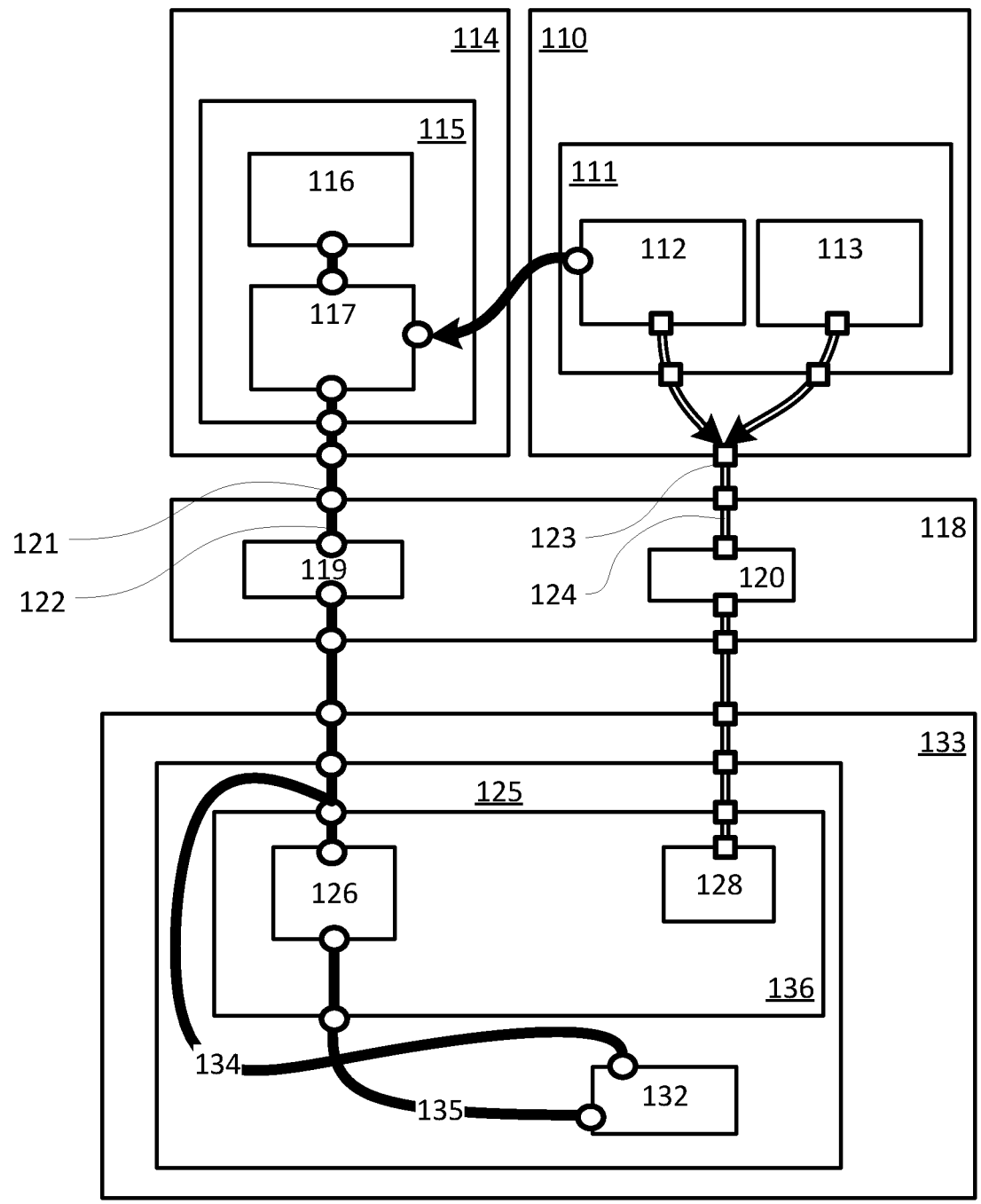
Figure 2.1

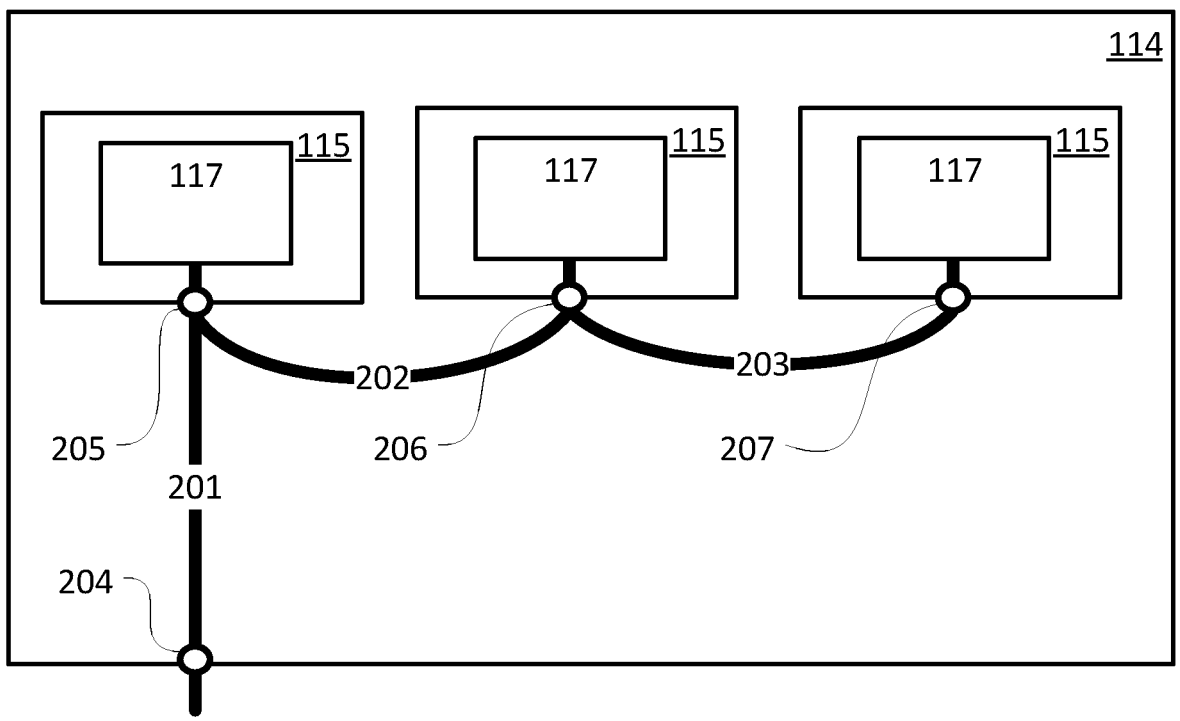
Figure 2.2
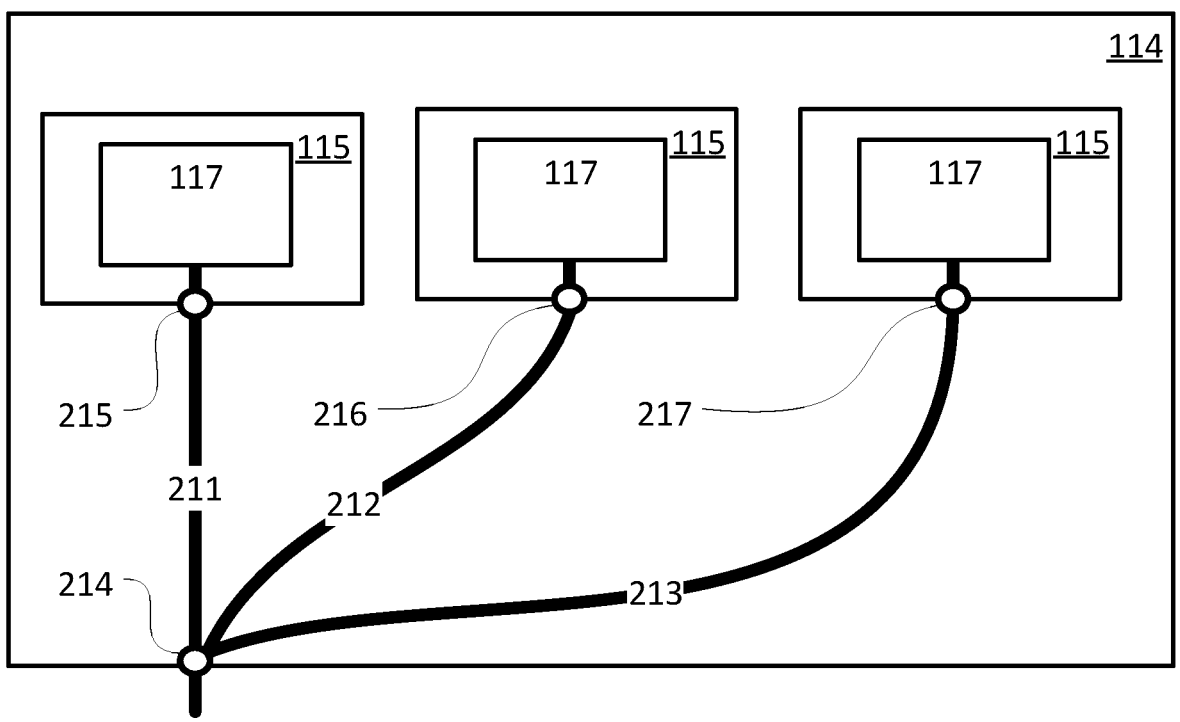
Figure 2.3

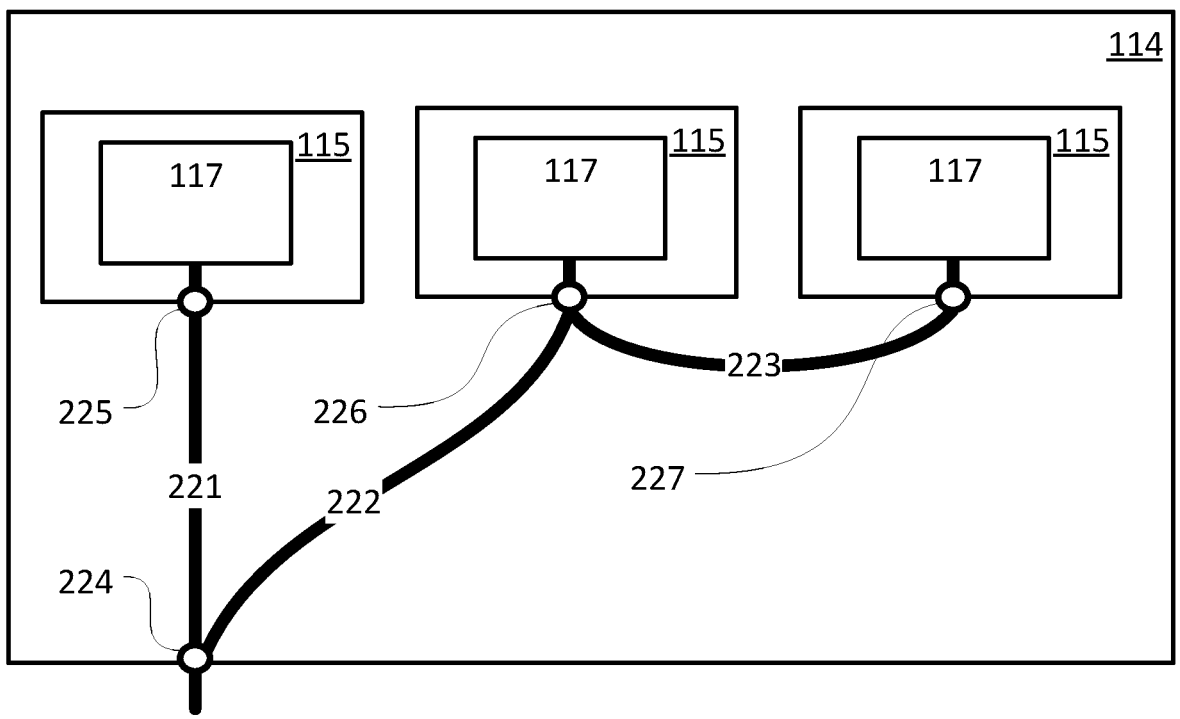
Figure 2.4

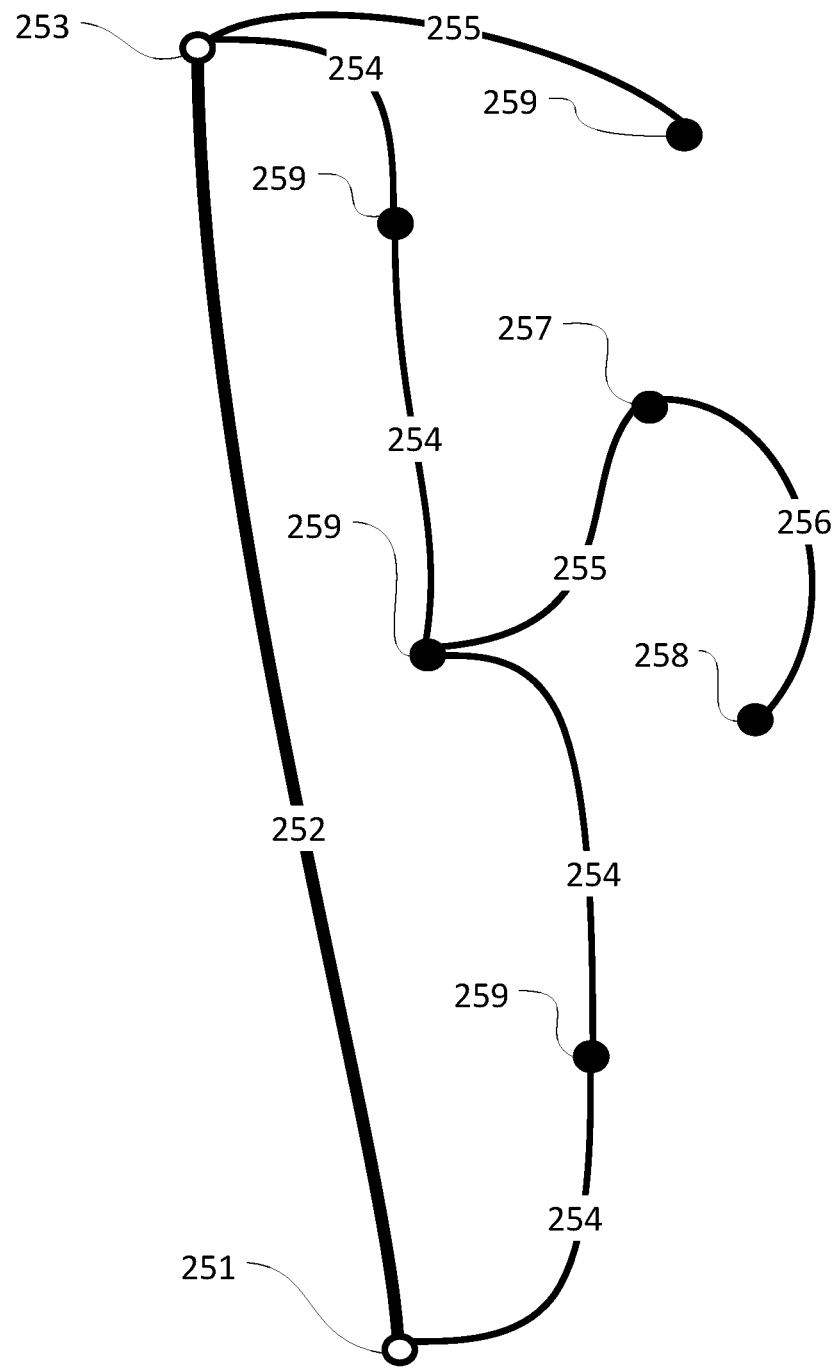
Figure 2.5

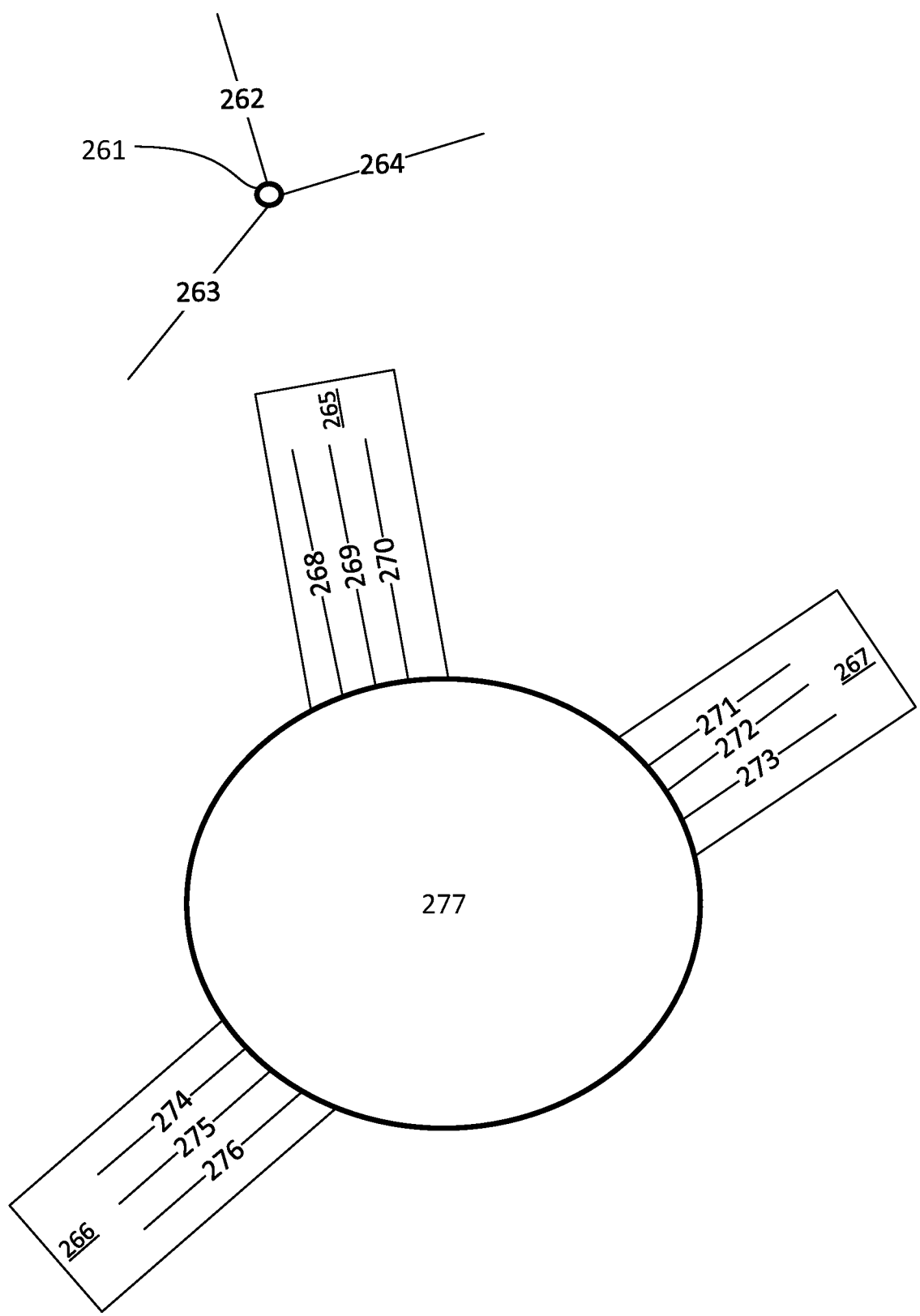
Figure 2.6

OPTICAL METHOD AND DEVICE FOR MONITORING A MEASUREMENT OBJECT

FIELD OF INVENTION

The present invention relates to a measurement technique utilizing optical devices for at least a part of a measurement device.

BACKGROUND

Measurement of a property of a measurement object is required in many technical fields. Such properties may be measured by electrical measurement methods.

In many technical areas, the use of electric measurement methods may be difficult, for example in areas having large electrical or magnetical disturbances or areas having high moisture or high temperatures.

Optical measurement technics may be used in such difficult areas. Examples of measurement areas wherein optical measurement methods are beneficial are:

1) Medical appliances, in which electrical interaction is non-desirable;
2) Monitoring of buildings and infrastructure, such as temperature, moisture, loads, fire alarm, smoke;
3) Hazard areas such as watercrafts, petrochemical industries, nuclear power plants having high demands on fire hazards;
4) Mobile telephones in which small components are beneficial;
5) Clothing and body wear;
6) Measurement of high temperatures and moisture.

A conventional optical measurement device may comprise a source of light driven by electrical power provided by, for example batteries or the line voltage. The light is transmitted to an optical sensor via an optical fiber. The light from the optical sensor may be influenced by a measurement object, for example reflected or absorbed, resulting in an optical signal, which is transmitted to a detector via an optical fiber, which may be the same optical fiber as mentioned above. The detector converts the optical signal to an electrical signal, which is processed by a computer. The optical fiber may be long, so that any electrical devices are positioned remote from the measurement object. See for example the patent publication WO2013/147670A1.

Another optical measurement device is known from patent application WO2020/027716, which discloses a device for monitoring a measurement object, comprising: an active unit having a light source, emitting light with a wavelength spectrum, and an optical detector. An optical link passes the emitted light to a at least one passive unit. Each passive unit comprises a sensor and a selector for diverting the emitted light to the sensor. The sensor comprises a luminescent material being directly or indirectly affected by the emitted light diverted by the selector. The sensor is sensitive to an external influence by the measurement object for producing a modulated signal, which is passed to said detector via the optical link. The luminescent material may be a fluorescent material, which is directly irradiated by the emitted light from the light source.

However, the measured optical signal in the previously known devices may be very small, and may drown in "noise" in the form of stray light from the surroundings. In addition, the optical fibers or other means conducting the light may comprise imperfections causing light in the same spectrum as the measured optical signal. The measured optical signal may in some instances be less than 1:10000 of other light.

Thus, there is a need for a device that may separate the measured optical signal from error sources such as disturbing noise and interference from other light.

SUMMARY OF THE INVENTION

Accordingly, an object of the present invention is to mitigate, alleviate or eliminate one or more of the above-identified and below mentioned or other deficiencies and disadvantages singly or in any combination.

In an aspect, there is provided a device for monitoring at least one measurement object, comprising: at least one active unit having at least one optical detector; at least one optical link; at least one passive unit having at least one light source radiating radiated light, which is modulated by at least one external measurement influence emanating from said measurement object; wherein said optical detector receives said radiated and modulated light via said optical link; further comprising at least one energy link; at least one receiver unit in said passive unit; at least one energy source for sending at least one energy amount via said energy link to said receiver unit in said passive unit; and at least one optical moderator for moderating said radiated and modulated light in dependence of said energy amount received by said receiver unit. The energy link may be the same as said optical link.

In an embodiment, the device may further comprise at least one energy signature influencing upon said energy amount, whereby said energy signature is transmitted to said receiver unit and said optical moderator together with said energy amount for controlling said optical moderator for moderating said radiated and modulated light in dependence of said energy signature received by said receiver unit. The energy signature may be controlled by at least one information data, and said optical moderator being controlled in dependence of said information data.

In another embodiment, the energy source may be at least one of: light, photons, electric field, magnetic field, electromagnetic field, entanglement, elementary particles, electrons, atoms, molecules, charge, wavelength spectrum, pressure wave, share waves, radiation, temperature, pressure, mechanical energy, vibrations, gravitation.

In a further embodiment, at least one moderator memory may be arranged between said receiver unit and said optical moderator.

In a still further embodiment, at least a portion of said energy amount received by said receiver unit is transferred to said light source for causing said light source to radiate light.

In a yet further embodiment, the light source may receive energy via said optical link or via said energy link for causing said light source to radiate light.

In a further aspect, there is provided a method of monitoring at least one measurement object, comprising: emitting at least one energy amount by a transmitter unit; transferring said energy amount by at least one energy link; receiving said energy amount by a receiver unit of a passive unit; passing at least a portion of said energy amount to at least one light source for radiating light; modulating the light source or radiated light by an external influence from said measurement object for producing radiated and modulated light; transferring said radiated and modulated light to at least one detector for providing detector information; transferring an energy signature from said transmitter unit to said light source for moderating the radiated and modulated light information from the light source by said energy signature, for producing radiated and modulated and moderated light; conducting said detector information to a processor unit for discriminating said radiated and modulated and moderated light received by said detector from error sources, such as noise.

In an embodiment, the radiated and modulated and moderated light may be transferred to said detector via an optical link. The optical link may be the same as said energy link.

In a further embodiment, the energy signature may comprise an address signal for selection of a predetermined passive unit, which has been programmed to correspond to said address signal. The energy signature may be a pulsation of said energy amount at a low frequency, such as below 1000 kHz.

BRIEF DESCRIPTION OF THE DRAWINGS

Further objects, features and advantages of the invention will become apparent from the following detailed description of embodiments of the invention with reference to the drawings, in which:

FIG. 2.1 is a block diagram similar to FIG. 1 of the embodiment.

FIG. 2.2 is a block diagram of a portion of the embodiment of FIG. 1 showing splitters in a first configuration.

FIG. 2.3 is a block diagram similar to FIG. 2.2 showing splitters in a second configuration.

FIG. 2.4 is a block diagram similar to FIG. 2.2 showing splitters in a third configuration.

FIG. 2.5 is block diagram of a portion of the embodiment of FIG. 1 showing paths and subpaths.

FIG. 2.6 is a block diagram of a portion of the embodiment of FIG. 1 showing channels.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

Figure 1:
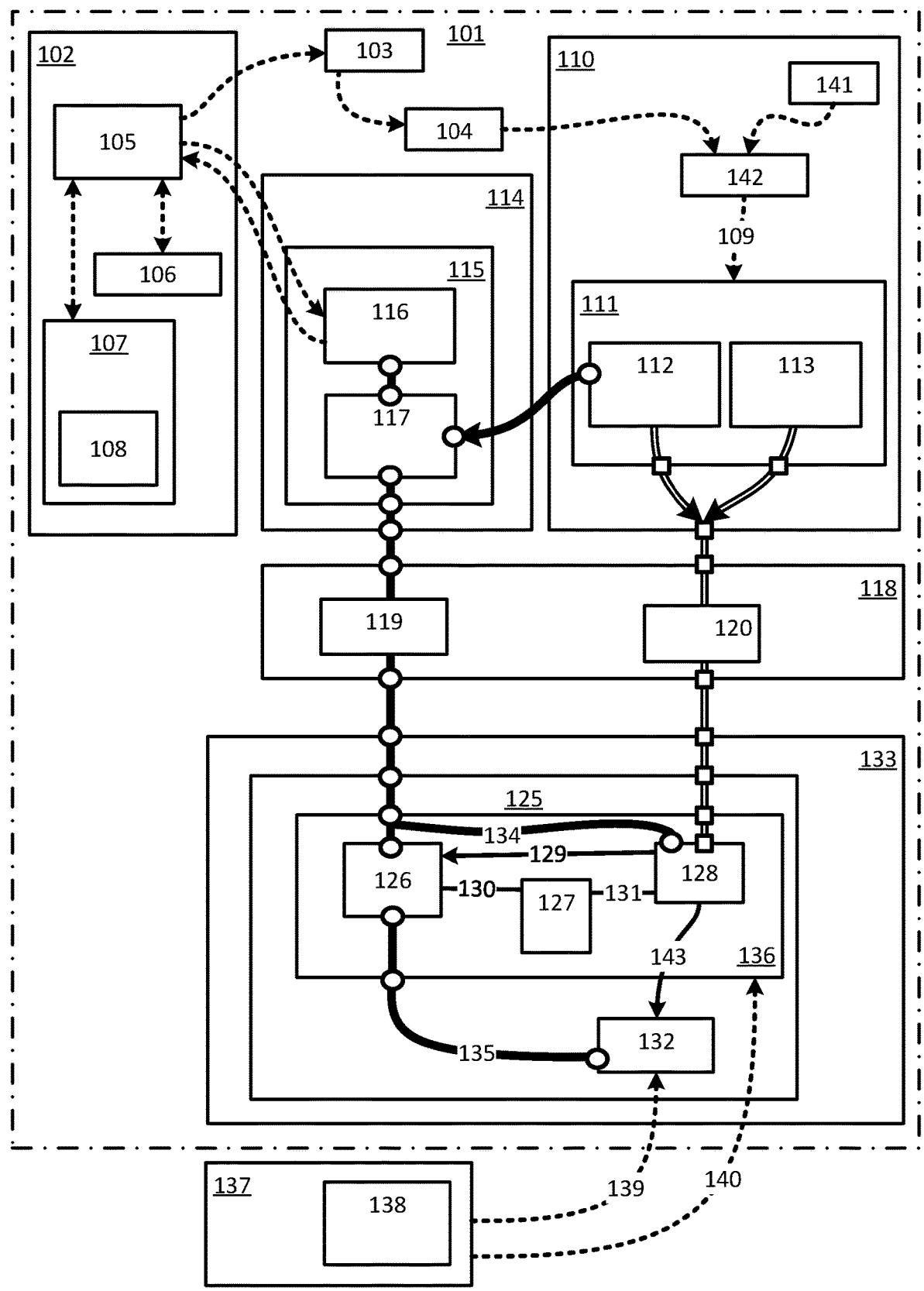
FIG. 1 is a block diagram of an embodiment of the invention.

FIG. 1 shows a first embodiment of a device of the present invention in block schema.

The first embodiment relates to an optical measurement device in which at least one optical measurement information is transmitted from at least one optical light source in at least one optical link, such as optical fibers, to at least one optical detector. The optical link may also transmit optical energy, for example for activation of a fluorescent material in the optical measurement device.

Since the optical measurement information may be very weak, it is important to reduce as much as possible error sources, emanating from for example cross-coupling; reflection, scattering and absorption in the optical fibers; fluorescence in the optical fibers, stray light, etc. Such error sources may be reduced by careful organization of the geometry of the device, shielding of the optical fibers and selection of suitable materials.

However, such measures may not be sufficient for robust detection of the optical measurement information, especially when the optical measurement information is weak. The device according to embodiments aims at providing additional measures so that the optical measurement information may be detectable even if it is close to the noise floor of the device, by providing an energy signature to the weak optical measurement information. A processor unit may use this energy signature for discriminating the optical measurement information from error sources such as noise. Other advantages may be that the energy signature may define the origin of the optical measurement information.

The device 101 comprises at least one processor unit 102, at least one active unit 115, at least one transmitter unit 111, at least one link 119, 120 and at least one passive unit 125. The device intends to measure at least one measurement property 138 of at least one measurement object 137 via at least one external measurement influence 139, 140. The active units 115 may be arranged in groups 114 of active units. The transmitter units 111 may be arranged in groups 110 of transmitter units. The links 119, 120 may be arranged in groups 118 of links. The passive units 125 may be arranged in groups 133 of passive units.

The passive unit comprises at least one light source 132, which radiates light modulated by the external influence 139. The radiated light is transmitted via an optical path 135 to an optical moderator 126. The optical moderator 126 receives a moderator influence 129 from a receiver unit 128. The receiver unit 128 receives moderator information from the transmitter unit 111. The optical moderator 126 exerts an influence upon the modulated light from the light source 132 in dependence of the moderator influence from the receiver unit 128, before or after the modulation.

In the passive unit 125, there may be arranged a moderator memory unit 127, which is connected to the receiver unit 128 by line 131 and with the optical moderator 126 via line 130.

The passive unit 125 comprises a light source and means for modulating and moderating the light radiated by the light source. However, the passive unit does not comprise an energy source for driving the light source, such as batteries. The energy for driving the light source is received by the passive unit from the transmitter unit.

The transmitter unit emits energy information, which serves two purposes.

1) The energy information should be transmitted to the passive unit in order to drive the light source to produce light to be used for the measurement. This is because the passive unit does not comprise a battery or other internal source for driving the light source. The transmitted energy may for example be UV light; NIR light; sound; magnetic field; electric field; electromagnetic energy, etc.

2) The transmitter unit emits an energy signature, which is used for discriminating the radiated light energy, after modulation by the external influence, from error sources, such as noise. The modulated light is further moderated by the energy signature. The energy signature may be a pulsation of NIR light or UV light.

Alternatively, the energy signature may be a sound by a specific frequency, which moderates the radiated and modulated light. For further alternatives, see below. The processor may identify this energy signature and use it for separating the radiated light from noise and other error sources. In addition, the energy signature may be used for providing an "address" for identification of a specific passive unit or group of passive units.

In an embodiment, the emitted energy may be coded by the energy signature and sent to the passive unit via the energy link. The passive unit receives the emitted energy by the receiver unit, which decodes the energy signature and moderates the radiated and modulated light in dependence of the energy signature. The processor may decode the detector signal for discriminating the signal from error sources.

The energy signature may be a low frequency compared to the energy frequency. A low frequency means below 1000 MHz, for example a pulsation with a frequency of below 1000 MHz. The frequency may be much lower if the system is mechanical, such as below 1000 kHz.

In the present specification, "passive unit" means a device, which comprises a light source and means for modulating and moderating the light radiated by the light source. The passive unit does not comprise an energy source for driving the light source, such as batteries. The energy for driving the light source is received by the passive unit. The passive unit may comprise storage members for temporary storing energy. The storage member may be a capacitor for storage of electric energy. The storage member may be mechanical for temporary storing mechanical energy.

In the present specification, "modulation" means that an external influence based on a measurement object property acts upon the light source in order to modulate the very light source or the light radiated by the light source in dependence of the external influence. The measurement object property to be measured is derivable from the modulated light. The external influence may be any influence inclusive no influence. The light source "radiates" light of any wavelength.

As an example, the external measurement property may be absorbance of visible light by a liquid, such as water, exudate, or blood from a dressing applied to a wound at the skin of a human being. Visible light from a light source is passed through the absorbent material and is attenuated by the absorbent material. The degree of attenuation means a modulation of the visible light. The external measurement property may be refraction index of a material outside a prism or cone of an optical fiber. If the material outside the cone is air, there is total reflection of the light and if the material is water, the total reflection ceases.

In the present specification "moderation" means that the moderator influences upon the very light source (before modulation) and/or the modulated light from the light source. The modulated and moderated light may have an energy signature which may be derivable by the device. There may be several moderators in each passive unit.

As an example, sound is emitted by the transmitter unit and received by a tuning fork. The tuning fork is connected to a mirror or prism arranged in the light path of the radiated light and moving the radiated light rays so that its amplitude changes in dependence of the frequency of the sound. The energy signature may be the frequency of the sound.

In the present specification, "monitoring" means overviewing a device for operation and performance, such as detecting at least one measurement information based on at least one external influence from at least one external object property of at least one external object. Monitoring may also include measurements, which are used for increasing the resolution and/or increasing the measurement accuracy. Monitoring may also include overview of the operability of the device or passive unit.

In the present specification, "energy path" and "optical path" means a member, which transports energy or optical energy from one fixed point to another fixed point, often inside a unit. The path may be a physical entity, such as a glass cylinder or a conductor or a metal rod, etc. but may as well be air, gas, vacuum or similar. The optical path is shown in the drawings as a bold line. The energy path (which may be an optical path) is shown by a double line.

In the present specification, "energy link" and "optical link" means a device, which transports energy or optical energy from one non-fixed point to another non-fixed point, often between two or several units, that are moveable in relation to each other. Examples of optical links are optical fibers. Examples of energy links are conductors, sound guides. Other examples of both are air, gas, vacuum etc.

In the present specification, "energy" means any type of energy, such as optical energy, magnetic field energy, electric field energy, sound energy, electromagnetic energy (other than optical).

In the present specification, "optical" means electromagnetic energy with a wavelength between 1 mm and 1 nm, including IR-light, NIR-light, visible light and UV-light.

In the present specification, "active unit" means a device which may receive light radiated by the light source of the passive unit.

In the present specification, "transmitter unit" means a device which may "emit" energy to the passive unit for activating the light source and for other purposes.

In the present specification, "processor unit" means a device which may control the active unit and/or the transmitter unit and which may receive information from the active unit. The processor unit comprises processor, memory and other logic required for the processor unit operation.

The active unit, transmitter unit and processor unit may be arranged in a single entity. Alternatively, the processor unit may be arranged to be connected wirelessly to the active unit and transmitter unit.

A passive unit may be passive in the sense that it does not do anything else than it is "programmed" to do and the "program" is not changed during a cycle. The "program" may be a physical layout of the passive unit. The program may be included in a memory unit and be performed by a controller, which may be a mechanical controller or viscoelastic controller or logics in which the controller or logics is physically controlled by viscoelastic properties. If the controller is electric or electronic, it may be powered by energy transmitted over an energy link or an optical link or both.

The passive unit may be positioned at a certain location, such as inside a dressing arranged at a wound at the skin of a human being. The passive unit will stay there during the entire measurement cycle, which may be from when the dressing is applied to the wound until the dressing is removed. The passive unit does nothing except to respond to certain interrogations sent to the passive unit. The passive unit does not need to be physically accessible during operation and during a measurement cycle, because there is no need to change anything of the passive unit.

A cycle is the smallest possible chain of events, which is necessary for generating a measurement. A cycle operates during a certain time, during which the chain of events is performed. At the end of the cycle time, a measurement may have happened. Such cycles may occur simultaneously, even for measurement at one and the same measurement object.

There may be a single passive unit. Alternatively, there are a plurality of passive units. These passive units may be arranged in groups of passive units 133, based on certain criteria. A group of passive units may comprise one or several passive units, and possibly zero passive units.

The passive unit 125 receives information or data or energy via at least one link. There are in principle two links to each passive unit, which are called optical link 119 and energy link 120. However, there may be only one link or more than two links, such as a group of links 118. Each link may be composed of a bundle of links, such as a bundle of optical fibers. If there is only one link, the link may be air, gas or vacuum; or optical fiber.

The modulated information may be radiated light from light source 132, which is modulated by the measurement object property to be measured. In this case, the modulated, and also moderated, radiated light is transmitted from the passive unit 125 via optical link 119 to the active unit 115. The active unit 115 comprises an optical detector 116 arranged to detect the radiated light and convert the radiated light to electric information, which are conducted to a processor 105. The optical link 119 may be at least one optical fiber but may alternatively or additionally be other means capable of transmitting light at the wavelength of the radiated light, such as visible light. Such other means may be air, vacuum, or a cylinder filled with gas.

In the embodiment of FIG. 1, there is at least one energy link 120, which is connected to the receiver unit 128 of the passive unit. The energy link 120 may transmit energy from the transmitter unit 111 to the passive unit. The energy may be sound energy, magnetic energy, electric energy, electromagnetic energy or optical energy. The energy (of any kind) transmitted by the transmitter unit 111 may be directional or omni-directional. If the energy source is omni-directional, the energy is radiated in all directions. If the energy is directional, the energy is conducted or focused towards one or several passive units. There may be more than one transmitter unit 111 and there may be groups of transmitter units 110.

In the case of optical energy, there is already a optical link 119, which may be used for passing optical energy from an optical transmitter 112 to the receiver unit 128. In this case, a separate energy link 120 may be superfluous. In other embodiments, the energy link 120 is an optical link (optical fiber or omni-directional link) separate from optical link 119.

In the embodiment of FIG. 1, the transmitter unit 111 comprises an optical transmitter 112 and a non-optical transmitter 113. The transmitter unit 111 may comprise either at least one optical transmitter 112 or at least one non-optical transmitter 113. On the other hand, the transmitter unit 111 may comprise at least one optical transmitter 112 and at least one non-optical transmitter 113.

As indicated in FIG. 1, the optical transmitter 112 may transmit optical energy via the energy link 120 or alternatively or additionally via optical link 119, via a multiplexer 117 arranged in the active unit 115. The non-optical transmitter 113 can only transmit energy via the energy link 120.

The optical transmitter 112 may be arranged to generate optical energy, which is transmitted to a multiplexer 117 in the active unit 115. The multiplexer 117 directs the optical energy to the optical link 119 and further to the passive unit 125. The passive unit comprises a optical energy path 134, which receives the optical energy and transmits the optical energy to the receiver unit 128 and further to the light source 132 via optical energy path 143. The light source may use the optical energy for generating the radiated light.

The processor 105 is arranged to generate information data 103 in the form of at least one energy signature 104. The energy signature 104 controls an (electric) energy moderator 142 driven by an (electric) energy source 141. The (electric) energy moderator may transfer an (electric) energy amount 109 to the transmitter unit 111, which converts the (electric) energy amount to an energy (of another kind, for example sound) amount to be transferred to the passive unit 125 via the energy link.

The operation of the device may now be described.

The light source 132 radiates light that is modulated by the external measurement influence 139, for example absorbance or refraction index. The external influence may also be exerted on an moderator unit 136, as shown by arrow 140, for example the temperature of the measurement object may be conducted to the optical moderator.

The modulated light in an optical path 135 is moderated by the optical moderator 126 and transmitted by the optical link 119 to the optical detector 116 and further to the processor 105. The transmitter unit 111 transmits an energy amount via energy link 120 to the receiver unit 128. If the transmitter unit 111 is a sound transmitter having the energy signature 35 kHz, the receiver unit 128 may be a tuning fork tuned to 35 kHz. Other frequencies may be used.

The processor 105 may analyze the received radiated light. If the radiated light has a specific energy signature, the processor 105 may associate the radiated energy with the corresponding specific passive unit. The processor 105 further comprises a memory unit 106, which may store energy signatures and passive unit information and further information. The processor communicates with a at least one measurement result unit 107, which produces at least one result property 108.

Figure 3:
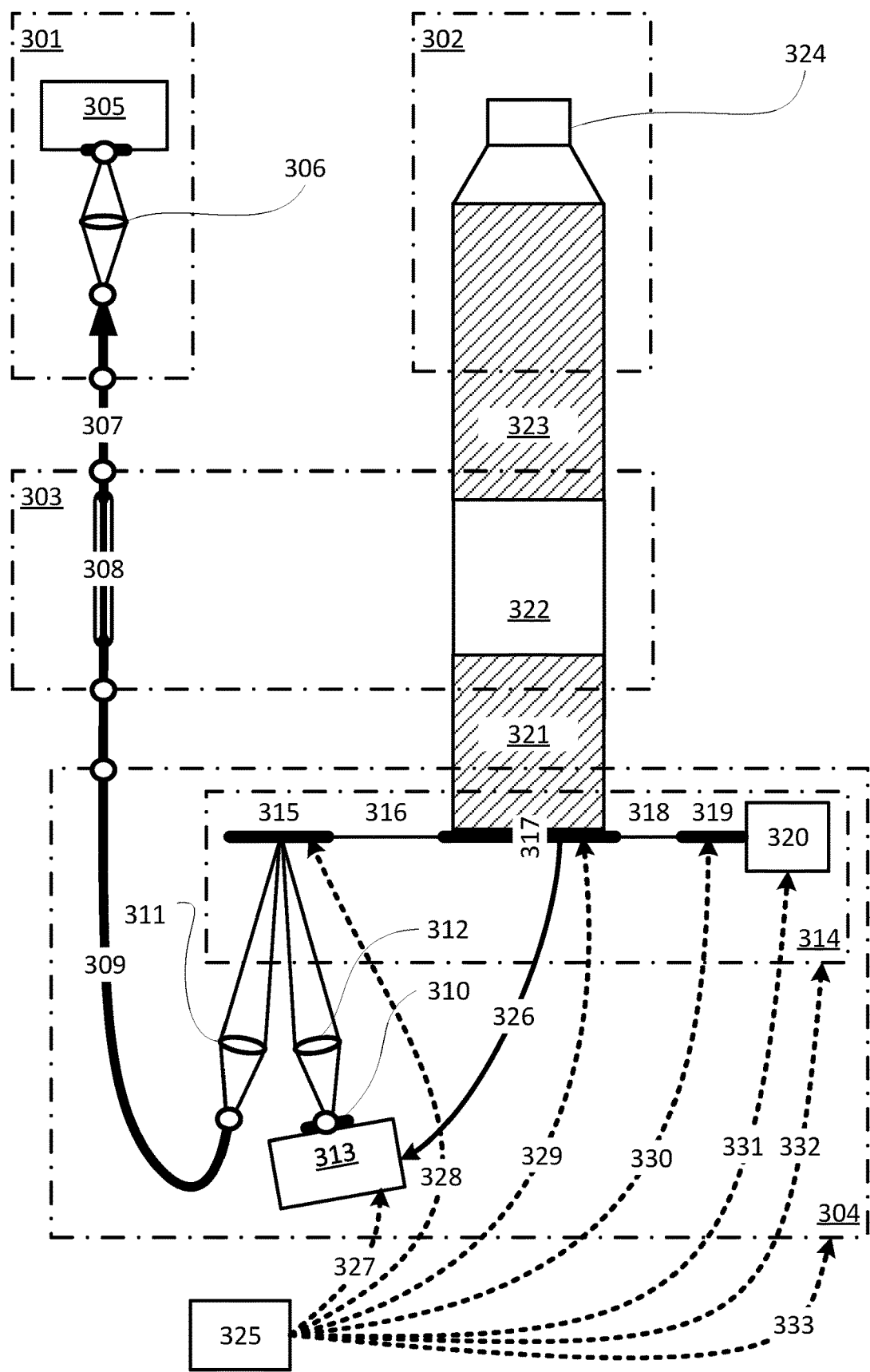
FIG. 3 is a block diagram of another embodiment of the invention.

FIG. 3 shows an embodiment in which a transmitter unit 302 transmits sound energy. The energy signature may be a sound frequency in the ultrasound area of above 20 kHz such as 35 kHz. A loudspeaker 324 converts an electric voltage with frequency 35 kHz to a sound wave with the same frequency. The sound wave is coupled to air in a sound path 323, which may form a horn construction, which directs the sound wave towards en energy link 322, which may be free air (omni-directional).

The sound wave is received by another sound path 321 which may be a funnel, which directs the sound wave towards a receiver unit 314 in a passive unit 304. The receiver unit 314 converts the sound energy to mechanical energy and may comprise a spring member 319 attached to a support member 320. A body member 317 having a predetermined mass is attached to the other end of the spring member, via an attachment 318. The other end of the body member 317 is connected to a mirror 315 via another attachment member 316. The spring member 319 and the body member 317 forms a resonance circuit, such as a tuning fork, with a resonance frequency, which may be tuned to the frequency of the energy signature (35 kHz). When a sound wave of the resonance frequency is received by the sound path 321, the body member resonates and moves or twists the mirror with the same frequency.

A light source 313 radiates modulated light 310, which is focused on the mirror 315 by a lens 312. The modulated light reflected by the mirror 315 is focused by another lens 311 to an optical path 309. When the mirror is in its rest position, the light rays from the mirror are aligned with the optical path 309. When the mirror vibrates, the light rays are moved in relation to the optical path 309 and hits the optical path only when the mirror is in its rest position. Thus, the radiated light received by the optical path 309 is moderated by the (double) frequency of the mirror. The modulated and moderated light in the optical path 309 is transmitted by an optical link 308, which may be an optical fiber in a group of links 303, to an optical path 307 and further to a detector 305 via a lens 306, arranged in the active unit 301.

The body member 317 may additionally comprise a device which converts a portion of the vibration energy to electric energy to be used for driving the light source 313. For example, an electric coil member may be arranged in connection with the body member, which may be made from a permanent magnetic material. The vibrations of the magnetic material produces a current in the electric coil member, which is transmitted to the light source 313 via a conductor 326. The light source 313 uses the electric energy for producing the radiated light.

The light radiated by light source 313 may be modulated by external influences 327 from an external object 325, for example absorbency. The external object may also cause external influences upon other members of the passive unit, such as the mirror 315 via external influence 328, the body member 317 via external influence 329, the spring member 319 via external influence 330, the support member 320 via external influence 331, the entire receiver unit 314 via external influence 332 and the entire passive unit 304 via external influence 333. Examples of external influences are temperature and viscosity for moving members, such as the mirror, the body member or the spring member.

Figure 4:
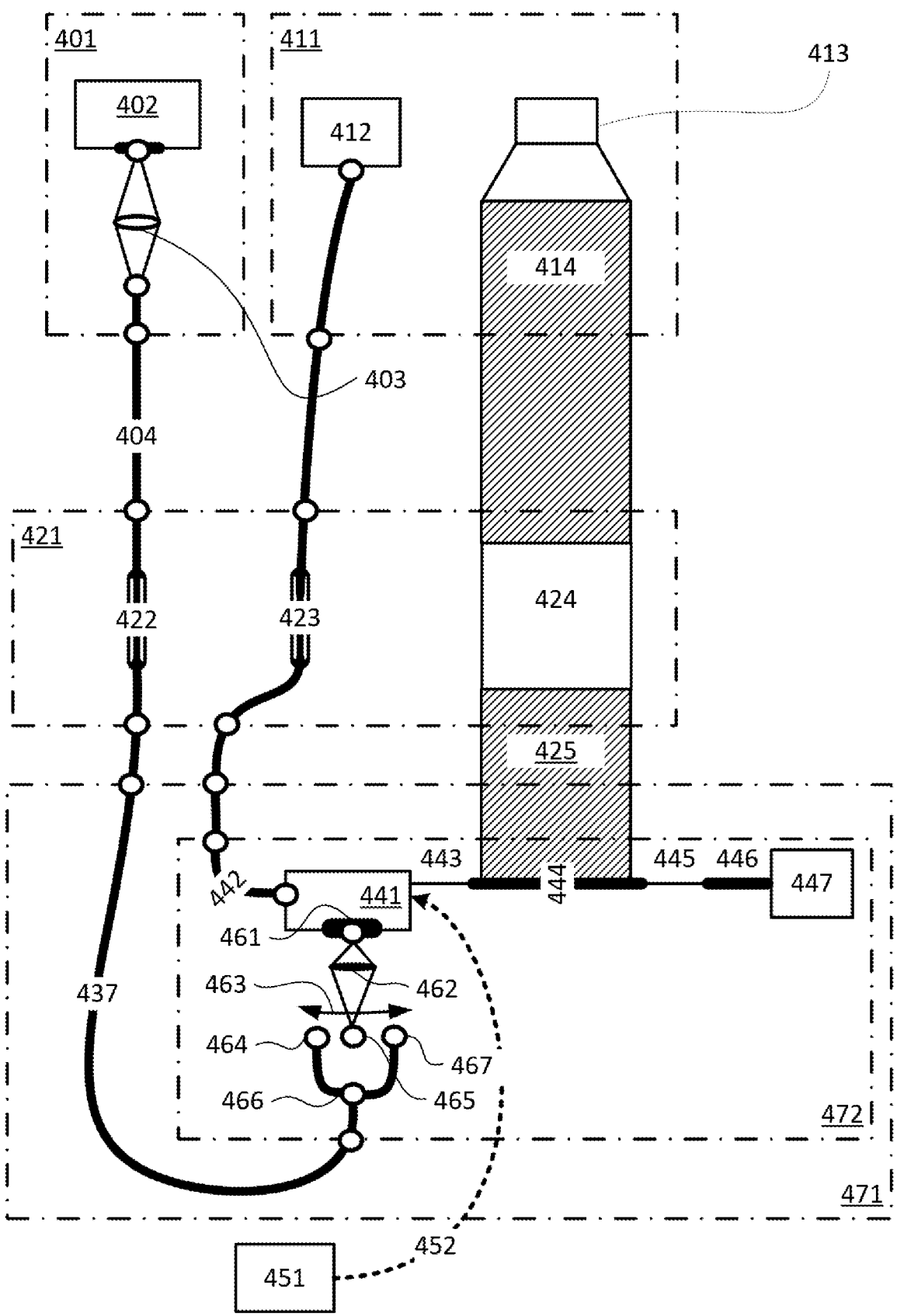
FIG. 4 is a block diagram of a further embodiment of the invention.

The sound energy may be replaced by another type of energy, such as magnetic energy as shown in FIG. 4. The magnetic energy is made to oscillate by a magnetic energy transmitter 413 and a varying magnetic field is transmitted by the transmitter, for example with a frequency of 1 Hz to 300 kHz. In this case, a body member 444 may be a ferro-magnetic material or a permanent magnet. The magnetic energy transmitter 413 in a transmitter unit 411 is arranged to transmit magnetic energy at a specific frequency, such as 45 kHz, via energy path 414, which may be a ferro-magnetic material. The magnetic energy is further transmitted via energy link 424 in a group of links 421, which may be an air gap or an air space. Finally, the magnetic energy is transmitted by an energy path 425 which may be a ferro-magnetic material. In a receiver unit 472 in a passive unit 471 the magnetic energy influences upon body member 444, which may be a permanent magnet. The body member 444 is supported by a spring member 446 via an attachment member 445. The spring is attached to a support member 447. The spring 446 and body member 444 forms a mechanical system with a specific resonance frequency, for example 45 kHz.

The body member 444 influences upon a light source 441 via an attachment member 443. The attachment member causes the light source to twist or vibrate. The light source comprises a light radiating member 461, which is influenced by the external influence 452 from external object 451 and radiates light modulated by the external influence. The radiated light from the light radiating member is focused by a lens 462 to a first light receiver member 464 or a second light receiver member 467 in dependence of the twisted movement of the light source, as shown by arrow 463. Any radiated light received by the first and second light receiving member 464 or 467 is combined by combiner member 466 and transmitted to an optical path 437 and further ultimately to an optical detector 402. In the middle position 465, or rest position, there is no light received by the first or second light receiving member 464 and 467. Thus, if body member 444 does not receive an energy signature, no optical information can be transmitted by the light source to the optical path 437. The light receiving members 464 and 467 act as an on/off switch, which enables operation only at receipt of an energy signature of the predetermined frequency. If the body member 444 vibrates with a frequency of 45 kHz, the light receiver members 464 and 467 will together receive radiated light moderated with a frequency of 90 kHz. This feature may be used by any of the other embodiments.

The body member 444 is attached directly to the light source 441, whereby the body member directly twists or vibrates or moves the light source 441. The light source may comprise a device which converts the vibrations to electric current, for example a piezo-electric material, whereupon the current drives the light source 441. Alternatively, the light source 441 may be made of a material which emits light when a force is exerted on the material, such as a piezoluminescent material.

Still alternatively or additionally, the light source 441 may receive optical energy from an optical transmitter 412 arranged in the transmitter unit 411 via an optical energy link 423 and an optical energy path 442. The optical transmitter 412 may generate NIR-light, which acts upon at least one current generator in the light source 441 and produces electric current, which drives an electroluminescent material in the light source. Alternatively, or additionally, the optical transmitter 412 may generate UV-light which acts upon a fluorescent material in the light source 441.

The light source 441 radiates light, which is modulated by the external influence 452 from the external object 451. The radiated light is focused by the lens 462 on the optical path 437. Since the light source is vibrated by the body member 444, the radiated light received by the optical path 437 is moderated by the vibration frequency of the body member 444. The radiated and modulated and moderated light from light source 441 is transmitted by the optical path 437 to an optical link 422 and further via an optical path 404 to a lens 403, which focuses the light to the optical detector 402 in an active unit 401.

The moderation unit may also be influenced by the external influence, for example temperature or viscosity.

Figure 5:
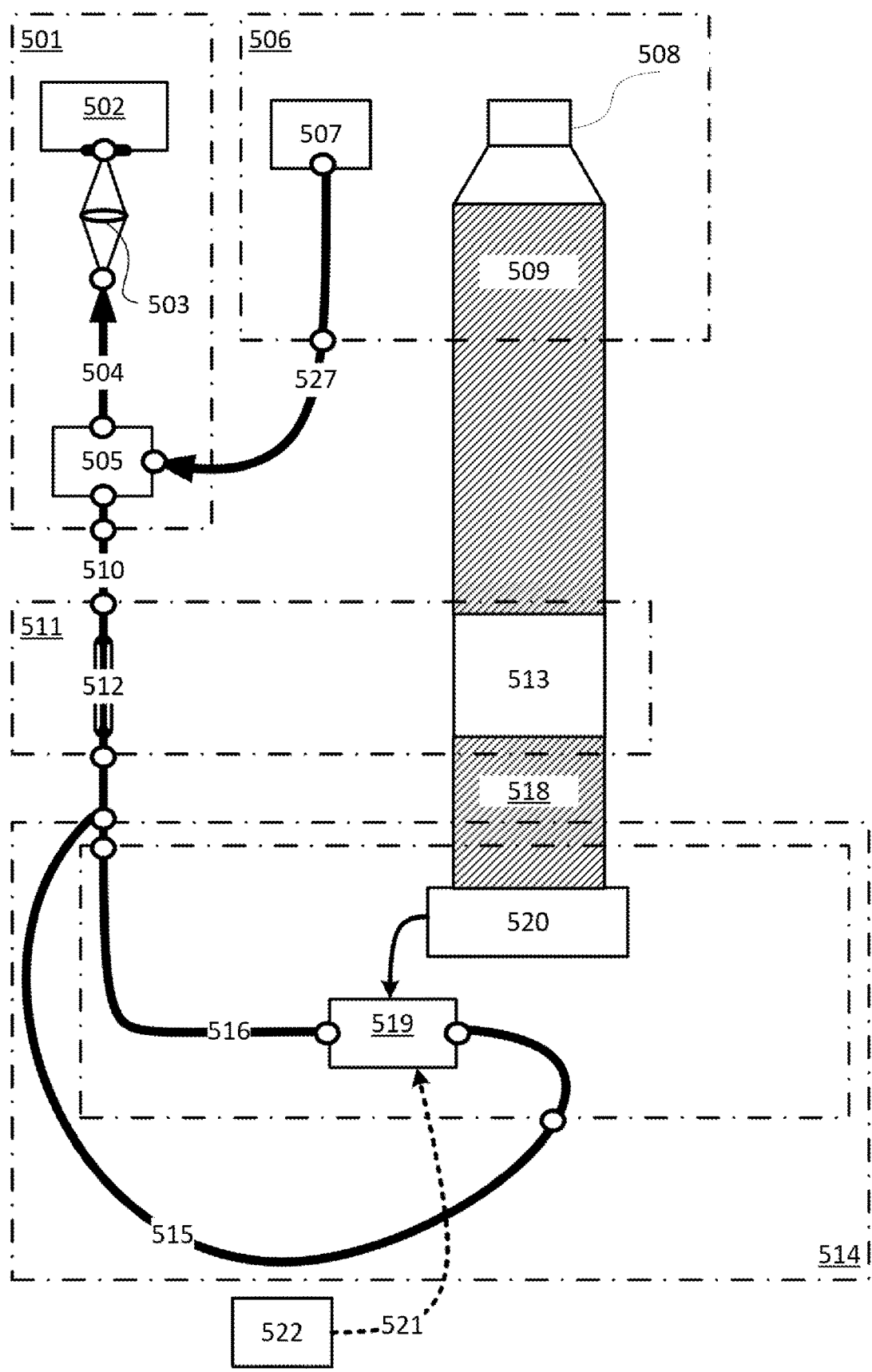
FIG. 5 is a block diagram of a still further embodiment of the invention.

FIG. 5 shows another embodiment of the device, in which a transmitter 508 in a transmitter unit 506 generates an electric field energy with a frequency of for example 55 kHz. This may be performed by supplying a positive voltage by the transmitter followed by a negative voltage, which are repeated with a frequency of for example 55 kHz. The electric field energy is transmitted by a energy field path 509, for example an electric conductor, to an energy field link 513 in a group of links 511, which may be air, and further to another energy field path 518 in the passive unit 514.

The energy field path 518 transmits the electric field energy to a coil or inductor in an energy receiver 520, which produces an electric current, which is conducted via a conductor to a light source 519. The electric current produces radiated light by acting on an electroluminescent material. The radiated light is moderated with the frequency of the electric field energy. In addition, the radiated light is exposed to an external influence 521 from a measurement object 522, whereby the external influence 521 modulates the radiated light. The radiated, modulated and moderated light is transmitted by an optical path 516 to an optical link 512, and further via an optical path 510, a multiplexer 505, an optical path 504 and a lens 503 to an optical detector 502 in an active unit 501. In this embodiment, the radiated light is first moderated by the energy signature and then modulated by the external influence. This feature can be used in all other embodiments.

The light source 519 may additionally receive optical energy from an optical transmitter 507 in the transmitter unit 506. The optical energy may be any light, such as NIR light or UV-light. The optical energy is transmitted via an optical energy path 527 to the multiplexer 505 in the active unit. The multiplexer 505 adds the optical energy to the optical energy path 510, whereupon the optical energy is transmitted via optical link 512 to an optical energy path 515 in the passive unit 514. The optical energy is transmitted via the optical energy path 515 to the light source 519, which may convert the optical energy to electric energy, which drives an electroluminescent material. Alternatively, the optical energy is used to directly produce radiated light by fluorescence.

The energy transmitter 508 is arranged to produce an electric field energy. Alternatively or additionally, the energy transmitter 508 may produce electromagnetic energy, in which case the energy receiver 520 may be an inductor/capacitor unit tuned to the frequency of the electromagnetic energy. The electromagnetic energy may have any frequency which may be received by the inductor/capacitor unit, such as electromagnetic energy with a wavelength from about 1000 meter to 1 mm.

Figure 6:
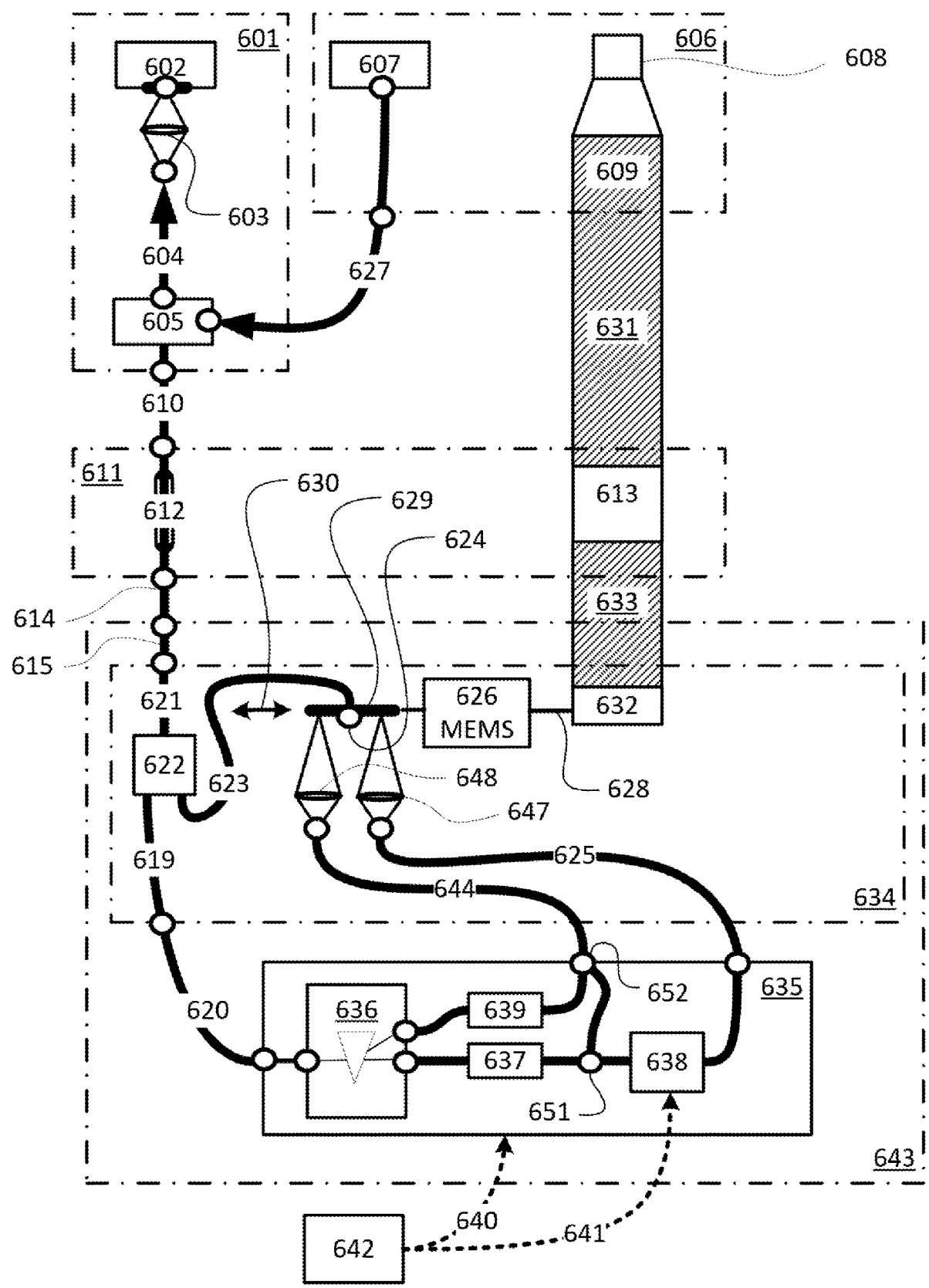
FIG. 6 is a block diagram of a yet further embodiment of the invention.

FIG. 6 shows a further embodiment, in which an electromagnetic energy transmitter 608 in a transmitter unit 606 is arranged to emit energy in the form of electromagnetic radiation, for example with a frequency of 850 MHz. The emitted electromagnetic energy is pulsed with a frequency of for example 25 kHz. The electromagnetic energy is transmitted to an energy path in the form of an antenna 609. There may be a director device 631, which directs the electromagnetic energy towards at least one passive unit 643. The antenna transmits electromagnetic energy via an energy link 613, which may be air, to an energy path 633, which may be another antenna directed to receive the electromagnetic energy. The electromagnetic energy is further transmitted to a receiver unit 632, comprising an inductor/capacitor, which is tuned to the frequency of the electromagnetic energy. Thus, a pulsating current is produced in the inductor/capacitor, which is conducted by a conductor 628 to a microelectromechanical system MEMS 626 arranged in a moderator unit 634.

The MEMS 626 is attached to a support member 629 supporting a radiated light receiver member 624. The MEMS 626 is arranged to move the support member 629 and the receiver member 624 back and forth as shown by arrow 630.

The transmitter unit 606 further comprises a UV light source 607 emitting UV light for example in at least one, such as four, wavelength spectra of 300-350 nm, 350-400 nm, 400-450 nm and 450-500 nm under the control of a processor unit (not shown). For example, in the second spectrum, there may be a first UV LED emitting UV light at wavelength 365 nm and a second UV LED emitting UV light at a wavelength of 385 nm. The UV light is transmitted via a light path 627 to a multiplexer 605 in an active unit 601. The multiplexer 605 transmits the UV light via an optical energy path 610 to an optical link 612, which may be an optical fiber in a group of links 611. The other end of the optical fiber is attached to the passive unit 643 via an optical energy path 621. The UV light is further transferred to a splitter/combiner 622 and further to an optical energy path 619 and another optical energy path 620 to a light source 635.

The light source 635 may be arranged with a selector 636, a fluorescent material 637 and an absorption member 638. The selector may be a prism, which refracts the light in dependence of the wavelength of the emitted UV light. The UV light influences upon the fluorescent material 637 and another reference fluorescent material 639 arranged in the light source. The angular position of the prism is adjusted in advance so that only light in one of the mentioned spectra is refracted to reach the fluorescent materials 637 and 639. Thus, light from UV LED 385 nm will reach fluorescent material 637 and light from UV LED 365 nm will reach the reference fluorescent material 639. UV-light with other wavelength outside 350-400 nm will be refracted by the prism, so that the UV light does not reach the two fluorescent materials 637 and 639. Other passive units respond to other UV wavelength spectra.

The radiated light from reference fluorescent material 639 is transmitted to an optical path 644. A lens 648 focuses the end of the optical path 644 to the support member 629 slightly to the left of receiver member 624. The radiated light from fluorescent material 637 is transmitted, via the absorption member 638 to an optical path 625. A lens 647 focuses the end of the optical path 625 to the support member 629 slightly to the right of receiver member 624. The absorption material 638 attenuates the light radiated by fluorescent material 637 via external influence 641 from external measurement object 642.

The operation is as follows. When the receiver unit 632 receives electromagnetic energy via the inductor/capacitor, it sends a command to the MEMS 626 to move support member 629 back and forth. When the support member is in its left position, the information from reference fluorescent material 639 is transmitted to receiver member 624 and when the support member is in its right position, the information from the absorbent fluorescent material is transmitted to receiver member 624. The information received by receiver member 624 is transmitted by optical path 623 further to splitter/combiner 622 and further to an optical detector 602 via optical path 621, optical path 615, optical path 614, optical link 612, optical path 610, multiplexer 605, optical path 604 and lens 603. The received information by the detector comprises a first portion, which is unaffected by the external influence and emanates from the reference fluorescent material 639, and a second portion which is affected by the absorbance of the external influence. In addition, there may be another external influence 640, for example temperature, which influences upon the entire light source.

In another embodiment, the reference fluorescent material 639 is omitted and a splitter 651 is connected to another splitter 652 via an optical path, and the radiated light from fluorescent material 637 unaffected by the external influence 641 is transmitted to the optical path 644 and functions as a reference.

Figure 7:
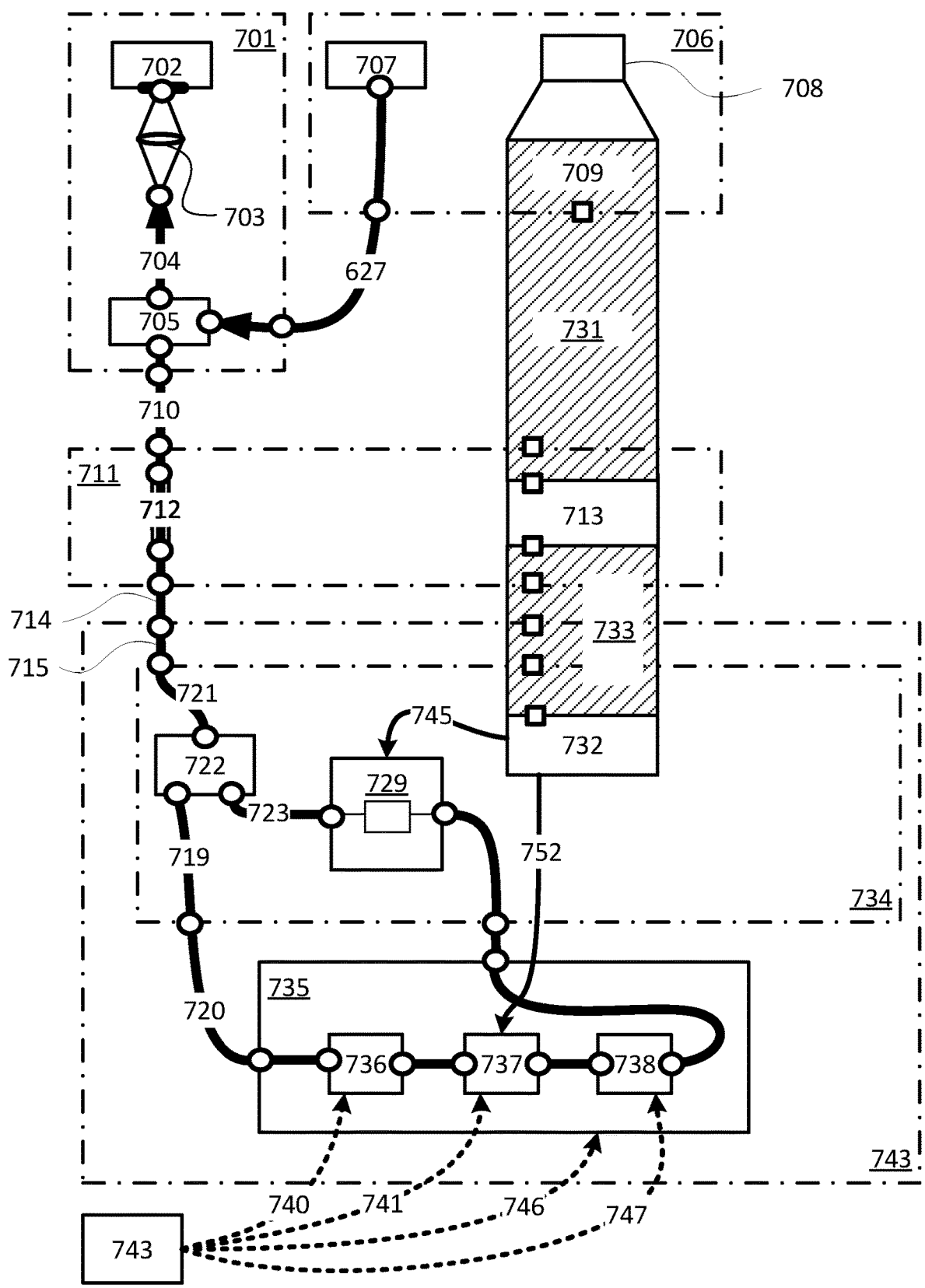
FIG. 7 is a block diagram of a still another embodiment of the invention.

FIG. 7 shows a further embodiment similar to the embodiment according to FIG. 6 and the same components have received the same reference numerals as in FIG. 6 but increased with 100. The transmitter 708 of transmitter unit 706 transmits electromagnetic energy via an antenna 709 and a director device 731 to energy link 713 and further via an energy path 733 to the receiver unit 732. The receiver unit 732 may be a tank circuit comprising an inductor/capacitor array. The voltage of the inductor/capacitor is conducted to the optical moderator 729 in a moderator unit 734 via a conductor 745. A light source unit 735 comprises a light source 737 receives optical energy from a receiver unit 732 via a conductor 752 and/or from an optical transmitter 707, via optical path 627, multiplexer 705, optical path 710, optical link 712, optical path 714, optical path 715, optical path 721, splitter/combiner 722, optical path 719, optical path 720, and an component 736, which may be a filter. The external object 742 exerts external object influences 740, 741, 746 and 747 as previously described. The modulated light passes via an absorbent component 738, which may be modulated by external influence 747 and further to the optical moderator 729. The optical moderator 729 may be floating crystals combined with polarization filters. There may be several optical splitters. Thus, each passive unit 743 may have several optical moderators 729 and several receiver units 732. There may be a sound energy receiver unit and an electromagnetic energy receiver unit. In addition, the transmitter unit may comprise several optical transmitters, for example a NIR light transmitter and a UV light transmitter. These components are interconnected by splitters/combiners.

There is an active unit 701 comprising an optical detector 702 receiving light from a multiplexer 705 via optical path 704 and a lens 703. The light produced by optical moderator 729 is passed via optical path 723 and splitter/combiner 722 further via optical path 721, optical path 715, optical path 714, optical link 712 in a group of links 711 and optical path 710 to the multiplexer 705.

Energy for driving the light source may as well be obtained by energy sources in the environment, such as vibrations and sound from ball bearings, electric motors, petroleum engines, traffic, jet motors, machines, sounds from a human, movements of arms, etc. Such natural sources can be used for driving the light source. Such energy sources may be used as a complement to energy produced by the transmitter unit and conducted to the passive unit via the energy link or optical link.

There are two types of links, energy link and optical link, both transmitting energy in one or both directions, where the energy link in all ways expands the possibilities of the optical link.

There are two types of sublinks, energy sublink and optical sublink, where the sublink is the key element in a link.

There are two types of paths, energy path and optical path transmitting energy in one or both directions.

There are two types of splitters, energy splitter and optical splitter, where said splitter also may be used as a combiner. The optical splitter is indicated by a circle in the drawings. The energy splitter is indicated by a square in the drawings. A sublink splitter is indicated by a filled circle in the drawings. An optical splitter is an optical component that may transmit incoming optical energy of an optical path/link into at least one other optical path/link. An optical splitter may also operate as an optical combiner that transmits incoming optical energy of at least one optical link/path to another optical link/path. The optical splitter/combiner is an optical component which may be embodied by different optical components, such as mirror, prism, filters etc.

Each one of the elements: a path, a link and a sublink, may transfer energy. Optionally, the elements may have one or several channels, where each channel transfers a portion of the energy, normally so that one channel does not affect other channels. However, optionally a portion of energy from one channel in an element is passed to another channel, in any direction, also in a new direction.

One or several splitters may exist as interface to some units. Any of the elements path, links and sublinks, may be connected to a splitter.

In a splitter, having et least two connecting elements, such as paths, links and sublinks, with several channels, a portion of the channels may also be connected individually to other channels in the splitter, where one way is to connect channel 1 from element 1 to channel 1 in element 2, and from channel 2 in element 1 to channel 2 in element 2, and so on.

FIG. 2.6 shows at the top an optical splitter 261 passing energy from/to three optical paths (or links) 262, 263, 264. FIG. 2.6 shows at the bottom an optical splitter 277 passing energy from/to three optical paths 265, 266, 267 in each three channels. The optical path 265 comprises three channels 268, 269, 270, which are interconnected with three channels 271, 272, 273 in the optical path 267, which in turn are interconnected with three channels 274, 275, 276 in the optical path 266.

A link and a sublink each have two ends, where at least one end is connected to a splitter. FIG. 2.1 shows an example of a device having several optical splitters 121, energy splitters 123, optical paths 122, energy paths 124, optical links 119, and energy links 120. The optical splitters are indicated by a circle and the energy splitters are indicated by a square.

When a link is connected between two splitters placed on separate units, additionally there may exist links, connected between one of the units, and/or additional units.

Additionally, a portion of energy entering a splitter in a channel may be reflected back in the same channel and in the same link as the energy came from.

In FIG. 2.2, an optical path 201 is connected between two optical splitters 204 and 205. Additionally, an optical path 202 is connected between the optical splitter 205 arranged at a first active unit 115 and another splitter 206 arranged at a second active unit 115. Additionally, an optical path 203 is connected between splitter 206 arranged at the second active unit 115 and another splitter 207 arranged on a third active unit (series configuration).

In FIG. 2.3 an optical path 211 is connected between two optical splitters 214 and 215. Additionally, an optical path 212 is connected between the optical splitter 214 and another splitter 216 arranged at a second active unit. Additionally, an optical path 213 is connected between the optical splitter 214 and another splitter 217 arranged on a third active unit (star configuration).

In FIG. 2.4 an optical path 221 is connected between two optical splitters 224 and 225. Additionally, an optical path 222 is connected between the optical splitter 224 and another splitter 226 arranged at a second active unit 115. Additionally, an optical path 223 is connected between splitter 226 arranged at the second active unit and another splitter 227 arranged on a third active unit (star and series configuration).

A sublink having two ends may have one end connected to another sublink end and/or connected to a splitter.

When several sublink ends are connected in a point, and have channels, optionally the channels in the sublinks, in the point may be connected, similar to the case in a splitter.

A link having two ends, each connected to a separate splitter, is characterized by comprising one or several sublinks, where there exists at least one route of the sublinks, connecting the two splitters. FIG. 2.5 illustrate that an energy link 252, for example an optical link arranged between two splitters 251 and 253, may be comprised of several sublinks 254 connected between sublink splitters 259. In addition, several sublinks 255 and 256 may divide from the sublink splitters 259 and are arranged between splitters 257 and 258.

A device may have at least one optical link and may have at least one "group of links", where a group of links comprises one or several links.

In a group of links, there exist et least one energy link or at least one optical link or both.

An optical link may pass light in both directions, such as UV-light, visible light and NIR light.

An optical link length can be very short or very long. An example, is between 3 millimeter to 100 meters (and up to 100 km). An optical link or sublink can be an optical fiber coiled as a spring or spiral, for being adjustable from 10% to 2000% of its nominal length. The coiled optical fiber may be flatted. When the optical link has many channels, this may be a bundle having many fibers.

Other examples of an optical link is a volume filled with a fluid or gas. A typical volume can be a tube. Gas pressure is typical 1 bar, limited in the range 10^-12 bar to 500 bar.

Another example of the optical link is a design preserving polarization when light is passed through, and/or a design effecting polarization when light is passed through, and/or a design effecting different optical modes when light is passed through, and/or a design where refractive index is different for different wavelengths.

An optical link may also be a ray of light passing in the air, gas or vacuum, without any boundary. An optical link may be constructed to withstand high pressures, vibrations, electromagnetic radiation and/or energetic particles.

An energy link expands the possibilities of the optical link to any kind of energy.

Examples of energy are: optical, sound, electromagnetic energy, magnetic field, electric field, vibration energy, acoustic energy, temperature energy, pressure wave energy, particle energy, charged particle energy, electron energy, chemical energy, mechanical structure energy.

Other examples of an energy link are: optical fibers in a bundle, conductor, microwave cavity, cavity, optical rays, rays, tubes with fluids, tubes, matter elements, air, vacuum, nerves, body fluids, mody materia, any liquid, solid material, conductors of any type, vacuum, etc.

An energy link can be very short or very long. An example, is between 3 millimeter to 100 meters (and up to 100 km). Another example is when links are placed in micro robots inside a body, or inside one or several electronic microchips, the length can be shorter in the range 0.1 mm to 10 mm.

An energy link transport all kinds of energy, in both directions, such as electromagnetic energy, magnetic energy, electric field energy, sound, vibration energy, pressure wave energy, acoustic energy, particle energy, charged particle energy, electron energy, light energy, photon energy, chemical energy, mechanical structure energy.

Other examples are when the energy is acoustics, where most of the energy is passed as an pressure and/or/shear wave through a media filled with matter, such as solid, liquid or gas. When gas is used, gas pressure is typical 1 bar, limited in the range 10^-4 bar to 500 bar.

The energy passing each energy link or each energy path may be moderated in the frequency domain or the time domain. For example, optical energy may be provided at one, two, three, four, five, six, seven, eight, nine or ten different wavelength spectra and/or being pulsed by a low frequency of for example 25, 35, 45 or 55 kHz.

In a sublink and/or a path, energy in the sublink and/or the path may be transported in the same ways as described above for a link, however sometimes over a length much shorter than the shortest lengths of the links in the device.

All the above examples and features and components can be combined in any desired manner.

One embodiment comprises one processor unit, one active unit and one transmitter unit arranged in one and the same enclosure. The transmitter unit transmits UV-light at wavelength spectrums of 300-350 nm, 350-400 nm, 400-450 nm and 450-500 nm via an optical link, which is an optical fiber, to each passive unit via splitters. In addition, the transmitter unit transmits a sound wave of a frequency of 35 kHz via an energy link, which is the air. There are four passive units each comprising a light source, each tuned to a wavelength spectrum of 300-350 nm, 350-400 nm, 400-450 nm and 450-500 nm, respectively. The passive units also comprises a mechanical receiver unit tuned to 35 kHz. The light source receives UV light from the transmitter unit and radiates light by fluorescence, which light is modulated by an external measurement influence and moderated by the sound wave frequency of 35 kHz via a mirror (FIG. 3). The radiated light is transmitted via the same optical fiber as mentioned above to an optical detector, which converts the optical energy information to electric information, which is supplied to the processor unit. The processor unit selects which of the four wavelength spectra that should be activated by the transmitter unit and put on the optical fiber, for example wavelength spectrum No. 2, 350-400 nm. The selection may be made by an optical component, such as a prism or filters. The sound transmitter is always transmitting sound energy at 35 kHz. Thus, the passive unit No. 2 receives UV-light which the passive unit passes to the light source to produce visible light via fluorescence. The visible light is transferred to the detector and further to the computer, which reads the modulation of the radiated light. Since the radiated light is moderated by 35 kHz, the processor unit may process the composite energy information from the detector and discriminate the radiated light information from noise and other error sources. The moderation by sound is used only for discrimination, not for addressing. The other passive units may be activated in the same manner, sequentially or simultaneously.

Another embodiment comprises the same components except that the UV light transmitter is replaced by a NIR light transmitter. Since NIR light cannot activate a fluorescent material, the light source instead comprises an electroluminescent material, such as a LED, which is activated by an electric current produced by an electric current generator driven by the NIR light. There is only one frequency of the NIR light, such as 850 nm. The sound generator is arranged to emit sound frequencies of 20 kHz, 25 kHz, 30 kHz and 35 kHz. The passive unit has each a mechanical receiver unit tuned to 20 kHz, 25 kHz, 30 kHz and 35 kHz, respectively. Each optical moderator is arranged so that in its rest position it diverts the radiated light off the light path 437, see FIG. 4 at 465. Thus, in the rest position, each passive unit does not pass any radiated light. When the light source is caused to oscillate, the radiated light is passed to the light path 437 with the frequency of the oscillations. The processor unit is arranged to command the transmitter unit to emit NIR light continuously, so that each passive unit receives NIR-light and activates each light source. The processor unit commands the sound transmitter unit to emit one of the selected sound frequencies, for example sound No. 2, 25 kHz. The mechanical receiver unit of the corresponding passive unit No. 2 having the tuned frequency of 25 kHz will start to oscillate. The light source activated by NIR-light will pass its radiated and modulated light with a frequency of 25 kHz to the detector and further to the processor unit. The processor unit may discriminate the useful information from noise and other disturbances. The other passive units may be activated in the same manner, sequentially or simultaneously.

The NIR-light energy receiver in the passive unit may convert the NIR-light to electric current. The electric current may charge a capacitor, so that a time lag occurs until the electric current is able to activate the electroluminescent material (LED). The time lag is dependent on the size of the capacitor and may be used by the processor unit for identification of the corresponding passive unit. This feature may be used by any one of the described embodiments.

In a further embodiment, the NIR light is pulsed with a low frequency, for example 40 kHz or 400 kHz or 400 MHz. In this case, the transmitter unit does not need to transmit sound energy, since the pulsation of the NIR light source will form the energy signature. The same principle of pulsation may be used for any of the other energy sources and by any one of the described embodiments.

In a yet further embodiment, there is no sound generator but only a UV-light source emitting light in four different wavelength spectrum, such as 300-350 nm, 350-400 nm, 400-450 nm and 450-500 nm. The processor unit causes the UV-light sources to pulsate with a frequency of for example 20 kHz. Thus, the corresponding passive unit will radiate light moderated by the pulsation frequency of the UV-light. This feature may be used by any one of the described embodiments.

In a still further embodiment, a combination of the first and the fourth embodiment is used, enabling 16 passive units to be selectively addressed. The radiated light is moderated by two frequencies, which makes it more easy for the processor unit to discriminate the information from noise. This feature may be used by any one of the described embodiments.

In still another embodiment, there is arranged a third energy transmitter in the form of a microwave transmitter having four (or a plurality of) transmitting frequencies. The energy receiver has a inductor/capacitor circuit tuned to each one of the four transmitted frequencies. In addition, there is a sound transmitter having four frequencies and a UV-light source having four wavelength spectra. Thus, 64 different passive units may be addressed separately. Further energy transmitters may be used. This feature may be used by any one of the described embodiments.

When a NIR light transmitter is used, there is a converter in the passive unit converting the NIR light to electric energy, such as a solar cell. The solar cell may be connected to a capacitor, which is slowly charged by the solar cell until a threshold voltage is achieved, at which time the entire stored energy in the capacitor is discharged and results in a short duration light flash with high intensity. This feature may be used by any one of the described embodiments.

In yet another embodiment, there is arranged 16 passive units at a dressing arranged at a wound. Each passive units comprises an optical fiber ending in a cone so that light is reflected when the medium outside the cone of the optical fiber has a refraction index of about one (air), and is not reflected when the medium outside the optical fiber has a refraction index of above 1.3 (water, blood, exudate etc.). The cone is connected to a light source comprising a fluorescent material. The arrangement is approximately the embodiment according to FIG. 4, in which the optical links 422 and 423 are free air. There is an optical energy transmitter 412 transmitting NIR light via a reflector towards an optical energy path in the passive unit 442. There is also a sound energy transmitter 413 transmitting sound via energy link 424 at 16 different frequencies between 20 kHz and 50 kHz with 2 kHz increments. There is an active unit 401 comprising a detector 402, which receives radiated and modulated and moderated optical information via optical link 422, which is free air. The transmitter unit 411 and active unit 401 are arranged in a single enclosure. The enclosure is brought into vicinity of the dressing and is directed towards the dressing so that the NIR light impinges upon the dressing and activates all 16 passive units at the dressing so that the light sources 441 of each passive unit radiates light. The sound energy transmitter is activated to emit sound energy at the energy signature frequencies between 20 kHz and 50 kHz during 0.3 seconds for each frequency. When a passive unit having the corresponding resonance frequency receives its energy signature frequency, the light source 441 will start to oscillate and the radiated light will pass to the receiver members 464, 467 and radiated and modulated and moderated light will be transmitted via optical path 437 and optical link 422 (free air) to the detector 402. Only one passive unit at a time will transmit radiated light. It the environment around the passive unit is air, the detector will receive radiated light and if the environment around the passive unit is water, blood or exudate, the detector will receive no radiated light. Thus, if the detector receives less than 16 radiated light, the dressing is partly soaked with water etc., and may require to be exchanged. This feature may be used by any one of the described embodiments.

In a still another embodiment, approximately similar to the one described in the previous paragraph, the optical transmitter 412 transmits UV light instead of NIR light. The UV light is directed towards the dressing and is arranged to scan over the dressing so that only one passive unit at a time is activated. The sound transmitter 413 transmits a single energy signature frequency of 25 kHz for activation of the oscillation of the light source 441. This feature may be used by any one of the described embodiments.

In addition, binary information may be transmitted by using two frequencies, wherein 20 kHz representing "0", and 40 kHz representing "1". In a time sequence each frequency is transmitted a short time duration, whereby a binary message may be transmitted. Also, coding techniques for error corrections and/or addressing may be used.

The detector may be an array of 256*256 detector pixels, for example a CCD or similar two-dimensional receiver. Alternatively, a one-dimensional CCS receiver may be used with an array of 1*256 detector pixels, which is moved over the object. Reference points may be used for reference purpose. Different channels in the optical link/path may be directed towards separate pixels or groups of pixels.

When an optical splitter is placed as an interface to an unit, connected to an optical path, the splitter may for each channel comprise a small surface, where the light in such a surface may be passed further to pixels in a CCD detector optionally passing optical elements, or be scanned by a scanner monitoring one or several of said surface elements.

It may be an advantage to use a separate optical link for returning the radiated light from the light source and use another optical link if UV-light should be used. This is because the UV-light may activate small amount of fluorescent material in the optical fiber, which may emit light in the same wavelength spectrum as the light source, and thus increase the noise level. NIR-light does not cause fluorescence and does not cause as much noise as UV-light.

Each one of the units: processor unit, active unit, transmitter unit, optical link, energy link, passive unit, measurement object are placed in spatial volumes. The units may be placed close to each other or separated with a distance. In an embodiment, the units: processor unit, active unit, and transmitter unit are placed relatively close to each other. An example of distances between any two elements is between 3 mm up to the maximum length of any link in the device.

Each one of the spatial volumes are placed in an environment and may be described with environment properties of any kind. Examples are: pressure, temperature, viscosity, gas concentrations, liquid concentrations, atom concentration, atom structure, mechanical data, magnetic field, electric field, radiation, waves, charged particles, etc. Other environment properties may be derivatives from the mentioned environmental properties and any other environment properties. There exist many environment properties and the limitations for each property is limited in a range.

The device according to embodiments may be used for measuring different properties. A few properties are mentioned below. If a method to measure the property is not obvious, also such a method is described:

Pressure as absolute value or relative value between two separate volumes, taken in different directions, caused by any kind of interaction, for example: mechanical, fluid, gas, vacuum, electromagnetic, acoustics, chemical, and other quantity describing a physical state;

Force as absolute value or relative value between two separate volumes, acting on an object caused by any kind of interaction, measured by using optical absorption or shielding in a mechanical structure;

Torque as absolute value or relative value between two separated volumes, acting on an object caused by any kind of interaction;

Acceleration of an object, measured by using a reference mass and force measurement;

Velocity of an object, measured by integrating a measured acceleration;

Pressure of an object;

Displacement of an object measured by using optical absorption or shielding in a mechanical structure, or by integrating measured velocity;

Internal Stress of an object, measured by using optical absorption or shielding in a mechanical structure and measured by using force measurement in small structures orientated in different directions;

Refractive Index measured in a volume, or at an interface;

Optical Transmission;

Optical Absorbance;

Optical Reflection;

Direction Wave Vector, evaluating the main energy direction in an optical energy transportation, measured by arranging small light transmission cavities in different directions and to measure optical transmission in each of them;

Charge close to a volume is measured;

Electric Field close or passing a volume is measured;

Current close or passing a volume is measured, measured by using ohms law and measure electric field;

Magnetic Field close or passing a volume measured;

Magnetic Flux Density close or passing a volume measured;

Resistivity close or in a volume measured, measured by moving the measured material itself in the information path 107a''' modulating the charged particle generator 1108;

Concentration of a species close or in a volume measured, measured by a having a reactive quenching the radiated fluorescence wavelength spectra, where reactive binds to the species, also measured by optical absorption in one or a purity of wavelength spectra;

Reactions Rate of a chemical compound.

A few embodiments of measurement objects are given below:

In a 1:st embodiment, liquid filling level detection and optionally blood detection is performed in a dressing placed over a wound outside the human body. It is desired to measure how much liquid a wound dressing has absorbed relative maximum absorption in some relevant volumes, and as an option to detect if a portion of blood above warning or alarm levels is present in relevant volumes, wherein the liquid information is passed to a user as warning information, and wherein blood detection is sent either as warning or as an alarm information to a user.

In a 2:nd embodiment, it is desired to monitor blood leaks from a venous needle of a dialyzing system. An arterial and a venous needle are inserted in an artery/venous fistula. If the venous needle is accidentally withdrawn, a large blood loss may occur if not discovered.

In a 3:rd embodiment based on an extension of first embodiment Also, other indicators are interesting when measuring in a dressing and therefore other properties such as: temperature, glucoses, ketones, proteins, bacteria, inflammation, can be measured.

In a 4:th embodiment, measuring health status in both human and animals, it is desired to measure health properties for having a draft indication of a patent health status, where the passive units can be placed in a variety of places like: a wound dressing, in a mobile phone, in clothing, in public environments, on exercising tools, in vehicles. Also properties such as, glucoses, ketones, proteins, bacteria, inflammation, can be measured.

In a 5:th embodiment, health status device taking measurement around skin, where most measurements are done above and below the top skin surface, typical +/−15 mm, as an option information is passed from volume below the skin to sensors on top of skin. Here needles can be used, specifically can micro needles be used. Also properties such as: temperature, glucoses, ketones, proteins, bacteria, inflammation, can be measured.

In a 6:th embodiment, health status device taking measurements inside the body, where also some measurements can be placed just outside the body. Typical measured properties are: movement, temperature, pulse, blood pressure, substances, nerves, blood species, proteins, cells, bacterizes, virus, vibrations.

In a 7:th embodiment, system status is measured in many kind of power systems, such as power production facilities, electric devices, ignition system, electronic devices, production plants, gearboxes, any kind of bearings, any kind of system where bearings exists, also in many power transmission paths such as cables and tubes, where energy exists in many ways such as electric, nuclear, vapor, chemicals, batteries. As an example the following properties are interesting to measure: temperature, mechanical stress, humidity, electric field, magnetic field, velocity, temperature, wherein measurement can be performed without electrical interference in hazard and high temperature volumes.

In an 8:th embodiment, system status is measured in environments, such as buildings, infrastructure, biological systems, underwater systems, information systems. As an example the same properties as mentioned in embodiment 7 are also here of interest to measure.

In a 9:th embodiment, system status is measured in any kind of moving devices with a mass larger than 10 gram, such as trucks, cars, motorbikes, bicycles, airplanes, trains, tram, rockets, military flying robots, bullets. As an example, the same properties as mentioned in embodiment 6 are also here of interest to measure.

In a 10:th embodiment, system status is measured in any kind of movable device that interact with environment with a wireless communication system, such as mobile phone, smartphone, laptop. As an example, the same properties as mentioned in embodiment 6 are also here of interest to measure.

In an 11:th embodiment, system status is measured in any kind of potential hazard volumes, for example where risk for fire and explosions exists. As an example, the same properties as mentioned in embodiment 6 are also here of interest to measure.

In a 12:th embodiment, measurement in human vital organs, such as brain, heart, lung, liver. As an example, the same properties as mentioned in embodiment 4 are also here of interest to measure.

In a 13:th embodiment, as embodiment 7, however limited to only in bearings or in systems where bearings exist.

In an 14:th embodiment, as embodiment 7, however limited to only usage in gearboxes.

In an 15:th embodiment, as embodiment 7, however limited only to usage in ignition systems.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment, it is not intended to be limited to the specific form set forth herein. Rather, the invention is limited only by the accompanying claims and other embodiments than those specified above are equally possible within the scope of these appended claims.

The invention claimed is:

1. A device for monitoring at least one measurement object, comprising:
    at least one active unit having at least one optical detector;
    at least one optical link;
    at least one passive unit having at least one light source radiating radiated light, the radiated light being modulated by at least one external measurement influence emanating from said at least one measurement object; wherein said optical detector receives said radiated and modulated light via said optical link;
    at least one energy link;
    at least one receiver unit in said passive unit;
    at least one energy source for sending at least one energy amount via said energy link to said receiver unit in said passive unit, whereby at least a portion of said energy amount is passed to said least one light source causing the at least one light source to radiate the radiated light;
    at least one optical moderator for moderating said radiated and modulated light in dependence of said energy amount received by said receiver unit;
    at least one energy signature influencing upon said energy amount, whereby said energy signature is transmitted to said receiver unit and said optical moderator together with said energy amount for controlling said optical moderator for moderating said radiated and modulated light in dependence of said energy signature received by said receiver unit.

2. The device according to claim 1, wherein said energy link is the same as said optical link.

3. The device according to claim 1, wherein said energy signature is controlled by at least one information data, and said optical moderator being controlled in dependence of said information data.

4. The device according to claim 1, wherein said energy source is at least one of light, photons, electric field, magnetic field, electromagnetic field, entanglement, elementary particles, electrons, atoms, molecules, charge, wavelength spectrum, pressure wave, share waves, radiation, temperature, pressure, mechanical energy, vibrations, gravitation.

5. The device according to claim 1, wherein at least one moderator memory is arranged between said receiver unit and said optical moderator.

6. The device according to claim 1, wherein said light source receives energy via said optical link or via said energy link for causing said light source to radiate light.

7. A method of monitoring at least one measurement object, comprising:
    emitting at least one energy amount by a transmitter unit;
    transferring said energy amount by at least one energy link;
    receiving said energy amount by a receiver unit of a passive unit;
    passing at least a portion of said energy amount to at least one light source for radiating light;
    modulating the light source or radiated light by an external influence from said measurement object for producing radiated and modulated light;
    transferring said radiated and modulated light to at least one detector for providing detector information;
    transferring an energy signature from said transmitter unit to said light source for moderating the radiated and modulated light information from the light source by said energy signature, for producing radiated and modulated and moderated light;
    conducting said detector information to a processor unit for discriminating said radiated and modulated and moderated light received by said detector from error sources.

8. The method according to claim 7, wherein said radiated and modulated and moderated light is transferred to said detector via an optical link.

9. The method according to claim 8, wherein said optical link is the same as said energy link.

10. The method according to claim 7, wherein said energy signature comprises an address signal for selection of a predetermined passive unit, which has been programmed to correspond to said address signal.

11. The method according to claim 7, wherein said energy signature is a pulsation of said energy amount at a low frequency, such as below 1000 KHz.

* * * * *